United States Patent [19]

Winter et al.

[11] Patent Number: 5,977,077
[45] Date of Patent: Nov. 2, 1999

[54] XANTHONE ANALOGS FOR THE TREATMENT OF INFECTIOUS DISEASES

[75] Inventors: Rolf Walter Winter, Portland; Michael Kevin Riscoe, Tualatin; David J. Hinrichs, Lake Oswego, all of Oreg.

[73] Assignee: Interlab Corporation, Lake Oswego, Oreg.

[21] Appl. No.: 08/619,063

[22] Filed: Mar. 20, 1996

Related U.S. Application Data

[63] Continuation-in-part of application No. 08/520,694, Aug. 28, 1995.

[51] Int. Cl.$^6$ .......................... A61K 31/70; A61K 31/435
[52] U.S. Cl. ............................. 514/23; 514/25; 514/27; 514/32; 514/42; 514/43; 514/277; 514/279; 514/290; 514/297; 514/430; 514/432; 514/437; 514/449; 514/451; 514/453; 514/454; 514/503; 514/185; 549/223; 549/388; 549/390; 549/392; 549/393
[58] Field of Search .......................... 544/150; 514/183, 514/455, 23, 25, 27, 32, 42, 43, 277, 279, 290, 297, 430, 432, 437, 449, 451, 453, 454, 503, 185; 549/383, 223, 388, 390, 392, 393

[56] References Cited

U.S. PATENT DOCUMENTS

| | | | |
|---|---|---|---|
| 3,346,579 | 10/1967 | Sheehan et al. | 260/279 |
| 3,639,612 | 2/1972 | De Long et al. | 424/276 |
| 3,714,194 | 1/1973 | Ulrich | 260/335 |
| 3,755,593 | 8/1973 | Adams et al. | 424/283 |
| 3,829,578 | 8/1974 | Fleming et al. | 424/283 |
| 3,887,574 | 6/1975 | Ellis et al. | 260/308 |
| 3,947,594 | 3/1976 | Randall | 424/331 |
| 3,948,920 | 4/1976 | Nabih | 260/288 |
| 3,953,602 | 4/1976 | Shemano | 424/283 |
| 3,957,986 | 5/1976 | Carr et al. | 424/248 |
| 3,985,783 | 10/1976 | Johnson et al. | 260/465 |
| 4,015,017 | 3/1977 | Gazave et al. | 424/331 |
| 4,284,627 | 8/1981 | Raether et al. | 424/229 |
| 4,290,954 | 9/1981 | Onogi et al. | 260/335 |
| 4,335,046 | 6/1982 | Horner | 549/392 |
| 4,539,412 | 9/1985 | Archer | 549/27 |
| 4,585,876 | 4/1986 | Fischer et al. | 548/423 |
| 4,661,607 | 4/1987 | Koga et al. | 549/383 |
| 4,816,479 | 3/1989 | Koga et al. | 514/455 |
| 4,996,230 | 2/1991 | Gapinski | 514/454 |
| 5,070,085 | 12/1991 | Markham | 514/161 |
| 5,093,372 | 3/1992 | Uedo et al. | 514/687 |
| 5,281,620 | 1/1994 | Denny et al. | 514/455 |

OTHER PUBLICATIONS

The Merck Index, Tenth Edition, p. 689 (entry 4656)(1983).
Bentue–Ferrer et al., "Comparative Evaluation of Scavenger Properties of Exifonem, Piracetam and Vinburnine," Laboratory of Clinical and Experimental Pharmacology, pp. 323–328 (1988).

Descombe et al., "Determination of Exifone in Human Plasma and Urine by High–Performance Liquid Chromatography with Electro–Chemical Detection," *J. Chromatogr.* 496:345–353 (1989).
Hafuri et al., "Mechanism of Inhibition of Reverse Transcriptase by Quinone Antibiotics—II. Dependence on Putative Quinone Pocket on the Enzyme Molecule," *J. Antibiotics* XLI:1471–1478 (1988).
Porsolt et al., "Antagonism by exifone*, a new cognitive enhancing agent, of the amnesias induced by four benzo–diazepines in mice," *Psychopharmacology* 95:291–297 (1988).
Vennerstrom and Eaton, "Oxidants, Oxidant Drugs, and Malaria," *J. Med. Chem.* 31:1269–1277 (1988).
Barbare and Raynal, "Hépatite aiguë associée á la prise d'axifone (Adlone®)," *Therapie* 45:47–52 (1990).
Chichmanian et al., "Exifone: quatre case d'hépatite," *Gastroenterol Clin. Biol.* 13:428–429 (1989).
Denjean et al., "Nouveautés en Hépatotoxicité Médicamenteuse," *Ann. Gastroentérol. Hépatol.* 26:293–298 (1990).
Larrey et al., "Hépatites probablement dues á l'exifone (Adlone®)," *Gastroenterol Clin. Biol.* 13:397–400 (1989).
Ouzan et al., "Atteintes hépatiques aiguës graves a l'exifone," *Therapie* 45:436–437 (1990).
Pateron et al., "Hépatite mortelle probablement due á l'exifone (Adlone®)," *Gastroenterol. Clin. Biol.* 14:294–295 (1990).
Ghosal et al., "Chemical Constituents of Gentianaceae XXIV: Anti-*Mycobacterium tuberculosis* Activity of Naturally Occurring Xanthones and Synthetic Analogs," *J. Pharm. Sci.* 67:721–722 (1978).
Hambloch and Frahm, "QSAR With the Tuberculostatic Activity of Polyhydroxy Xanthones and Their $^{13}$C–NMR Chemical Shifts," *Eur. J. Med. Chem.* 20:71–77 (1985).
Hostettmann et al., Strategy in the Search for New Biologically Active Plant Constituents, Proceedings of0 the Phytochemical Society of Europe, v. 37, Phytochemistry of Plants Used in Traditional Medicine, K. Hostettmann, A. Marston, M. Maillard, and M. Hamburger (eds). Oxford Science Publishers (1995).
Sultanbawa, "Tetrahedron Report No. 84—Xanthonoids of Tropical Plants," *Tetrahedron* 36:1465–1506 (1980).
Wang et al., "Swertifrancheside, an HIV–Reverse Transcriptase Inhibitor and the First Flavone–Xanthone Dimer, from *Swertia franchetiana*," *J. Nat. Prod.* 57:211–217 (1994).

*Primary Examiner*—Lila Feisee
*Assistant Examiner*—Michael Pak
*Attorney, Agent, or Firm*—Klarquist Sparkman Campbell Leigh & Whinston, LLP

[57] ABSTRACT

Therapeutic compositions for the treatment of infectious diseases are disclosed. These compositions comprise xanthones and xanthone derivatives, such as 2,3,4,5,6-pentahydroxyxanthone. Also disclosed are methods for the treatment of infectious diseases using such compounds.

6 Claims, 1 Drawing Sheet

FIG. 1

XANTHONE ANALOGS FOR THE TREATMENT OF INFECTIOUS DISEASES

This is a continuation in part of U.S. patent application Ser. No. 08/520,694, filed Aug. 28, 1995, which is herein incorporated by reference.

ACKNOWLEDGMENT OF GOVERNMENT SUPPORT

This invention was made with partial support from the United States Government to Drs. Michael K. Riscoe an d David J. Hinrichs through the Veterans Affairs Merit Review System. The government may have certain rights to this invention.

TECHNICAL FIELD

This invention pertains to therapeutic compositions for the treatment of infectious diseases.

BACKGROUND OF THE INVENTION

Protozoan parasites cause diseases such as malaria, trypanosomiasis, Chagas' disease, leishmaniasis, giardiasis, and amoebiasis. These and other protozoan parasite diseases have historically occurred in tropical and sub-tropical areas where they cause widespread damage to human populations. Although they receive little attention in the Western world, protozoan diseases affect more people worldwide than diseases brought on by any other biological cause (Heyneman, 1988).

The global importance of just one parasitic protozoan disease, malaria, can be appreciated by considering that historically, roughly half of all people who have lived and died have died of malaria. Today, malaria remains the most destructive single infectious disease in the developing world. It is responsible for more human energy loss, more debilitation, more loss of work capacity, and more economic damage than any other human ailment facing the world today (Heyneman, 1988). The World Health organization estimates that 1 to 2 million deaths are caused by malaria each year in Africa alone; most of these are children under the age of five (World Health organization, 1991). In addition, over 300 million people worldwide are believed to be chronically infected, and each year nearly one third of these individuals will suffer acute manifestations of the disease.

Today, the pathologic capacity of protozoa is being increasingly demonstrated in the Western world among the victims of AIDS (Acquired Immunodeficiency Syndrome). AIDS depletes the immune system of affected individuals; this allows opportunistic agents which would be defeated by an active immune system to infect AIDS patients. Several protozoa have emerged as important opportunistic infections in AIDS patients including *Cryptosporidium parvum, Entamoeba histolytica, Giardia lamblia, Pneumocystis carinii* (which may be a fungal or protozoal pathogen), and *Toxoplasmosis gondii*.

Despite the prevalence and significance of protozoan infections, therapy for these diseases is generally poor or in need of improvement. Many chemotherapeutic agents used to treat protozoan infections are non-specific cytotoxins that are highly toxic and cause severe side effects in patients. However, these drugs are used because there are no better alternatives. For example, giardiasis and amoebiasis are treated using metronidazole (a nitroimidazole), but the use of this drug is clouded by its mutagenic potential (Campbell, 1986) and its adverse interaction with alcohol. For trypanosomiasis and leishmaniasis standard therapies (suramin, melarsoprol, and pentavalent antimonials) are dangerously toxic, occasionally fatal, and often ineffective (Mebrahtu, 1989; Grogl et al., 1992). Other drugs are becoming ineffective due to emerging resistance. In the case of malaria, effective therapy has previously been provided by chloroquine but its efficacy is now threatened by the rapid emergence of drug resistant strains of *Plasmodium falciparum*, the causative agent for the most severe, often fatal, form of the disease (Cowman, 1990). Other protozoal infections such as cryptosporidiosis or Chagas' disease have no proven curative agent.

The present invention is directed to new antiparasitic agents and methods of using known compounds as antiparasitic agents. The invention is also directed to compounds with broad-spectrum anti-microbial activity.

SUMMARY OF THE INVENTION

As a result of studies aimed at developing new antiparasitic agents, the present inventors have discovered that xanthones and a wide range of xanthone derivatives and structurally related compounds, as shown in formula X1, have potent anti-parasitic activity. The compounds have broad-spectrum anti-microbial activity, including anti-fungal activity against *Candida albicans*.

Formula X1:

wherein:

A is oxygen, substituted antimony (stibium), sulfur or N—R' wherein R' is H, OH, alkyl, haloalkyl, aryl or haloaryl; and $R_1$–$R_8$ are independently selected from the group consisting of H, OH, halogen, aryl, arylamine, alkyl, alkene, substituted alkyl (such as alkylamine, alkylthio and haloalkyl), amino, ester, ether and nitro groups and O-linked and C-linked carbohydrates.

Examples of substituted antimony include antimonial oxides and antimony substituted with hydroxy, chlorine, alkyl and aryl groups (e.g. SbCl, $SbCl_3$, SbOH, Sb(O)(OH)).

In another embodiment, A is oxygen, sulfur or NH, and $R_1$–$R_8$ are independently selected from the group consisting of H, OH, aryl, haloaryl, arylamine, alkyl, alkene substituted alkyl, halogen, amino, ester, ether and nitro groups.

In other embodiments, A is oxygen and $R_1$–$R_8$ are independently selected from the group consisting of H, OH, and acetoxy ($CH_3C(O)O$).

The formula X1 compounds encompass some compounds described for the first time herein.

In other embodiments, the compounds of the present invention include compounds according to formula X2:

Formula X2:

wherein A is oxygen, sulfur or NH, and $R_1$–$R_6$ are independently selected from the group consisting of H, OH, aryl, arylamine, alkyl, alkene substituted alkyl, halogen, amino, ester, ether and nitro groups. In particular embodiments of the present invention, the term "alkyl" refers to substituents having lower alkyl groups, i.e., $C_1$–$C_{10}$.

In preferred embodiments of the present invention, the formula X1 compounds are compounds according to the formulae:

Formula X3:

Formula X4:

wherein A is selected from the group consisting of oxygen, sulfur and NH, and $R_1$–$R_6$ are independently selected from the group consisting of H, OH or an ester group, such as $OCOCH_3$ or $OCO(CH_2)_3CH_3$ or a carbamate ester. In preferred embodiments, the $R_2$ and $R_5$ groups are esters. In yet other embodiments, A is oxygen and $R_2$–$R_5$ are all hydroxy; in further preferred embodiments, at least one of $R_1$ and $R_6$ are H.

In more preferred embodiments, the formula X1 compounds are compounds having the following formulae:

Formula X5:

Formula X5E:

Formula X6:

Formula X6E:

wherein A is oxygen, sulfur or NH and E is an ester. Specific examples of such compounds include 2,3,4,5,6-pentahydroxyxanthone; 2,3,4,5,6-pentaacetoxyxanthone; 2,3,4,5,6,7-hexahydroxyxanthone; 2,3,4,5,6,7-hexaacetoxyxanthone; 2,3,4,5,6-pentahydroxyacridone; 2,3,4,5,6-pentaacetoxyacridone; 2,3,4,5,6,7-hexahydroxyacridone; 2,3,4,5,6,7-hexaacetoxyacridone; 2,3,4,5,6-pentahydroxythioxanthone; 2,3,4,5,6-pentaacetoxythioxanthone; 2,3,4,5,6,7-hexahydroxythioxanthone; and 2,3,4,5,6,7-hexaacetoxythioxanthone.

In the most preferred embodiments, the formula 1 compounds are 2,3,4,5,6-pentahydroxyxanthone and esterified forms of this compound, including 2,3,4,5,6-pentaacetoxyxanthone and 2,3,4,5,6,7-hexahydroxyxanthone and esterified forms of this compound, including 2,3,4,5,6,7-hexaacetoxyxanthone.

The present invention thus includes compositions for the treatment of microbial diseases such as malaria, the compositions including a compound according to formula X1. Also included in the present invention is a method of inhibiting the growth of a microbial pathogen comprising providing a sufficient amount of a formula X1 compound and contacting the microbial pathogen with this compound. Such a method is applicable to inhibit microbial growth in vivo and in vitro. In one aspect, the present invention provides a method of treating a patient having a microbial infection, the method comprising administering to the patient a therapeutically effective amount of a compound according to formula X1.

DETAILED DESCRIPTION OF THE INVENTION

1. Definitions

The phrases "a xanthone according to formula X1" and "a xanthone derivative according to formula X1" refer to a compound having the following structure:

wherein:

A is oxygen, substituted antimony (stibium), sulfur or N—R' wherein R' is H, OH, alkyl, haloalkyl, preferably lower alkyl or lower haloalkyl wherein "lower" means 10 or fewer carbon atoms, aryl or haloaryl; and $R_1$–$R_8$ are independently selected from the group consisting of H, OH, halogen, aryl, arylamine, alkyl, substituted alkyl (such as alkoxy, alkylamine, alkylthio and haloakyl), amino, ester and nitro groups and O-linked and C-linked carbohydrates. In alternative embodiments, an alkyl substituent is a lower alkyl.

As used herein, the term "alkyl" encompasses alkanes, alkenes and alkynes, including branched forms, isomers and stereoisomers. The term "lower alkyl" refers to an alkyl having 10 or fewer carbon atoms.

The terms "ester" and "esterification" are used herein as ordinarily understood in the chemical arts, see, for example, Morrison and Boyd, *Organic Chemistry*, Allyn & Bacon, Inc., Boston, 1983, herein incorporated by reference. Thus, an ester may be formed by, for example, the combination of an alcohol and an organic acid, with the concurrent elimination of water. The process of forming an ester is termed "esterification." For example, the formula X1 compound 2,3,4,5,6-pentahydroxyxanthone may be esterified by reaction with appropriate acid anhydrides resulting in the net replacement of one or more hydroxyl substituents with ester substituents including, but not limited to: acetoxy ($OCOCH_3$); propionyloxy ($OCOCH_2CH_3$); and butyryloxy $OCO(CH_2)_2CH_3$) substituents. Esters produced in this manner may be generally represented by the formula $OCO(CH_2)_nCH_3$ wherein n is zero or a positive integer. In particular embodiments, the term "ester" as used herein refers to an ester wherein n is 1–10.

A "microbial pathogen" is a microorganism capable of causing disease in an animal. The term "microbial pathogen" includes bacterial, mycoplasmal, fungal and protozoan organisms. "Protozoan parasites" are a subclass of microbial pathogens, being protozoan organisms that are capable of invading, colonizing and, under appropriate conditions, causing disease in an animal. Examples of protozoan parasites include *Leishmania donovani, Plasmodium falciparum, Giardia lamblia, Trypanosoma gambiense* and *Trypanosoma cruzi*. See generally, Robbins et al., Pathologic Basis of Disease (Saunders, 1984) 273–75, 360–83.

A "microbial infection" is a disease caused by a microbial pathogen.

A compound having "anti-microbial activity" is a compound that is capable of inhibiting the growth of a microbial pathogen as determined in in vivo or in vitro assays of the kind normally employed to determine minimum inhibitory concentrations (MICs) or 50% inhibitory concentrations ($IC_{50}$) of an antimicrobial agent.

An "oxidant agent" is an agent having the ability to produce or liberate free radical oxygen species or to render parasites or their host cells more susceptible to oxygen radical attack, or having the capacity of oxidizing another compound. Examples of oxidant agents in this sense include ascorbic acid, hydrogen peroxide, tetracycline and gamma radiation.

2. Methods Employed for Determining Biological Activity

The anti-parasitic activity of the compounds of the present invention was determined using two different parasites: *Plasmodium falciparum*, a causative agent of malaria; and *Leishmania donovani*, a causative agent of leishmaniasis. The activity of the compounds against yeast was determined using *Candida albicans*.

A. Assay for anti-malarial activity

The D6 strain of *P. falciparum* was cultured in Group $A^+$ human erythrocytes and suspended at a 3.3% hematocrit in RPMI-1640 (Gibco, Grand Island, N.Y.) (containing 4 g/L glucose, 50 mg/L gentamicin and 10% group $A^+$ human serum), buffered with 25 mM HEPES and 25 mM $NaHCO_3$ (Larrey, 1989). Cultures were maintained at 37° C. in a gas mixture of 5% oxygen, 5% $CO_2$, and 90% nitrogen.

The in vitro anti-malarial activities of 2,3,4,5,6-pentahydroxyxanthone and other formula X1 compounds were measured by the [$^3$H]-ethanolamine incorporation method as described in Elabbadi et al., 1992, with minor modifications. [$^3$H]-ethanolamine was obtained from American Radiolabeled Chemicals, Inc., St. Louis, Mo. Experiments were conducted in 96 well plates in a total volume of 200 μl at a final red blood cell concentration of 3.3% (v/v). An initial parasitemia of 0.2 to 0.5% was attained by addition of normal uninfected red cells. Radiolabeled ethanolamine was added after 48 hours of incubation and the experiment was terminated after 72 hours by collecting the cells onto glass fiber filters with an automated multiwell harvester.

Stock solutions of the various formula X1 compounds were dissolved in DMSO at a concentration of 1 mM and diluted in complete medium (including 10% human serum) to provide 10× stock concentrations in the range of 1 to 10,000 nM. The concentration of the formula X1 compound giving 50% inhibition of label incorporation ($IC_{50}$) relative to control (i.e., drug-free) conditions was calculated from the dose-response curve.

B. Assay for anti-leishmania activity

*Leishmania donovani* was cultivated in Schneider's medium (Gibco, Grand Island, N.Y.) according to the methods described by Grogl et al. (1992). The in vitro susceptibility of *L. donovani* to formula X1 compounds was determined using the radiolabeled thymidine uptake assay essentially as described by Grogl et al. (1992). Briefly, promastigotes were cultivated at 25° C. in Schneiders medium supplemented with 20% inactivated fetal calf serum and 100 μg/mL of gentamicin. Cells were maintained in log phase by seeding at $1\times10^6$/mL with subculturing when cultured densities approached $4\times10^7$/mL before reaching their maximal density. For the assay, early log phase promastigotes were counted on a hemacytometer and resuspended at a concentration of $1–2\times10^6$ cell/mL in assay media (Schneiders medium plus 10% fetal bovine serum). Ten-fold serial dilutions of each test compound were prepared as described above and added to 180 μL of the parasite suspension. After incubation for 24 hours at 25° C., methyl-$^3$H-thymidine was added to each sample for a final concentration of 1–2 μCi per well. Each sample was then incubated for an additional 18 hours prior to harvesting. After this incubation time, each sample was aspirated onto a filter mat, washed thoroughly with deionized water, dried and then counted in a scintillation counter with scintillation cocktail.

C. Assay for anti-Candida activity

The minimum inhibitory concentration (MIC) of formula X1 compounds against a clinical isolate of *Candida albicans* was determined using the following method. As used herein MIC represents the concentration of formula X1 compound that completely inhibits growth of *Candida albicans* over the course of a 15–18 hour incubation period. The determination of this concentration is made by visual inspection; there is no visible growth in a tube containing the MIC of the formula X1 compound whereas visible growth is present in tubes containing sub-MIC concentrations of the compound.

*Candida albicans* was grown to midlog-phase in Luria-Bertani broth (10 grams Bacto-tryptone, 5 grams Bacto-yeast extract and 10 grams NaCl per liter) and then inoculated into sterile test tubes containing LB broth to an initial density of $10^3$/ml. The formula X1 compound to be tested is dissolved in dimethylsulfoxide (DMSO) at a concentration of 10 mM and added to each tube at serial dilutions (1 $\mu$M, 10 $\mu$M, 25 $\mu$M, 50 $\mu$M, 100 $\mu$M and 0 $\mu$M). The tubes are incubated at 35° C. for 15–18 hours and then visually inspected.

3. Production of 2,3,4,5,6-pentahydroxyxanthone in Parasitized Erythrocytes Treated with Rufigallol and Exifone As disclosed in U.S. patent application Ser. No. 08/520,694, rufigallol (1,2,3,5,6,7-hexahydroxy-9,10-anthraquinone) is a potent anti-parasitic agent and, when rufigallol is combined with exifone (2,3,3',4,4',5'-hexahydroxybenzophenone), a synergistic effect is observed. The synergy between rufigallol and exifone is noted to produce about a 350-fold increase in potency against malaria Plasmodium parasites.

Figure 1:
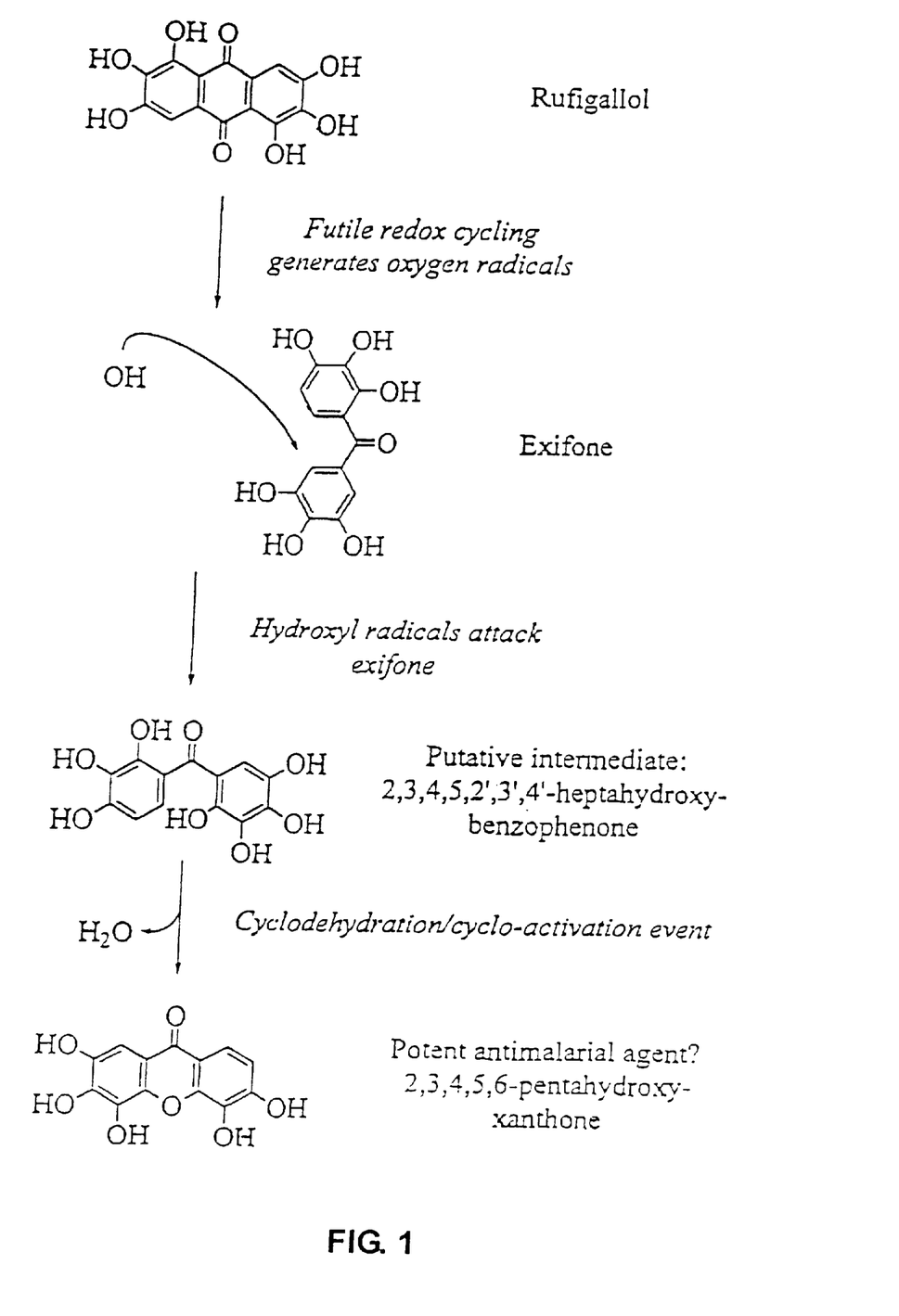
FIG. 1 illustrates a proposed mechanism for the formation of 2,3,4,5,6-pentahydroxyxanthone from the metabolic activation of exifone by rufigallol within a red blood cell infected with the Plasmodium parasite.

One aspect of the present invention is the discovery that rufigallol and exifone interact in the parasitized erythrocyte to yield 2,3,4,5,6-pentahydroxyxanthone, and that this compound is a potent anti-malarial agent. FIG. 1 shows a possible mechanism by which 2,3,4,5,6-pentahydroxyxanthone could be produced when rufigallol and exifone are present in a parasitized erythrocyte. Basically, rufigallol is proposed to enter the parasitized erythrocyte, leading to the formation of hydrogen peroxide in a manner similar to the well-documented redox cycling behavior of hydroxynaphthoquinones. In the presence of large quantities of adventitious iron or iron chelates, such as heme, (liberated as a result of the Plasmodium parasite digesting hemoglobin, Atamna and Ginsburg, 1993), hydrogen peroxide is readily decomposed to hydroxyl radicals (Goldstein et al., 1993; Aust et al., 1985). These highly reactive radicals are proposed to attack exifone and transform the diphenyl compound into 2,3,4,5,6-pentahydroxyxanthone.

As reported in application Ser. No. 08/520,694, the anti-malarial activity of exifone can be potentiated by a very wide range of oxidant agents, including ascorbic acid, artemisinin and doxorubicin. This observation is consistent with the mechanism proposed above. The production of 2,3,4,5,6-pentahydroxyxanthone in the proposed reaction scheme was confirmed by incubating exifone with ascorbic acid in the presence of iron salt and oxygen in a buffered solution at 37–40° C. (the "Udenfriend system," Brodie et al., 1954; Maisant et al., 1983; Udenfriend et al., 1954). Samples were removed from the reaction at various time points, lyophilized and extracted with acetone. The solubilized products were then methylated by addition of excess potassium carbonate and dimethylsulfate in acetone and analyzed by gas chromatography-mass spectrometry. A peak corresponding to the methoxy derivative of 2,3,4,5,6-pentahydroxyxanthone was detected.

4. Synthesis and Anti-Microbial Activity of 2,3,4,5,6-pentahydroxyxanthone

The formula X1 compound 2,3,4,5,6-pentahydroxyxanthone is produced using the following method.

A mixture of 1,2,3-Trimethoxybenzene (1.48 g) and 2-hydroxy-3,4,5-trimethoxybenzoic acid (2.00 g) is stirred in 40 ml of ~9% solution of $P_2O_5$ in methanesulfonic acid at room temperature in a stoppered flask for 4 hours. The 2-hydroxy-3,4,5-trimethoxybenzoic acid was obtained by the method of Mayer and Fikentscher (Mayer and Fikentscher (1956) *Chem. Ber.* 89:511) from 3,4,5-trimethoxybenzoic acid by bromination and then copper-catalyzed replacement of bromine (by OH) of 2-bromo-3,4,5-trimethoxybenzoic acid. The resultant orange mixture is poured onto crushed ice (500 ml) producing an unfilterable gummy precipitate. This crude product is then subjected to base-catalyzed ring closure by heating in a beaker in 100 ml of 40% ethanol and 10 ml of 10N NaOH just below boiling point. As the mixture reaches 80° C., a white flocculent product appears. The temperature is maintained just below the boiling point and the volume is kept constant by addition of water. After 5 hours, the supernatant is bright yellow and a mass of the precipitate has formed. Heating is continued for 4 more hours. Cooling, filtering (by suction) and washing with water afforded 1.37 g of analytically pure 2,3,4,5,6-pentamethoxyxanthone (yield approximately 45% relative to benzoic acid). This base-catalyzed ring closure is illustrated below:

2,3,4,5,6-pentahydroxyxanthone is then obtained by boron tribromide treatment (200 ml of a 0.8 M solution in $CH_2Cl_2$) as the pentamethyl ether (0.45 g) is stirred at room temperature for 24 hours. After this period, the solution is poured into 100 ml of water and stirred for approximately 45 minutes before the precipitate is collected by centrifugation. The supernatant is then decanted, the precipitate is shaken with water and centrifuged again. The final product is obtained by freeze-drying of the wet precipitate to produce an orange powder (0.290 g, 81%).

The anti-malarial activity of 2,3,4,5,6-pentahydroxyxanthone was determined by the method described above. The $IC_{50}$ was determined to be 0.4–0.5 $\mu$M. Chloroquine, a standard anti-malarial agent has an $IC_{50}$ in this assay system of approximately 0.02 $\mu$M.

The anti-leishmanial activity of 2,3,4,5,6-pentahydroxyxanthone was determined by the method described above. The $IC_{50}$ was determined to be approximately 5 $\mu$M or 0.001 mg/ml. Mangostin, a naturally occurring xanthone, exhibited an IC$_{50}$ of 1 μM (or 0.00041 mg/ml) in this same system. Grögl et al. (1992) report that two commonly used anti-leishmanial drugs, Pentostam and Glucantine, have IC$_{50}$ values in the range of approximately 0.1–2 mg/ml.

The MIC of 2,3,4,5,6-pentahydroxyxanthone against *Candida albicans*, determined using the method described above was found to be approximately 37.5 μM. This corresponds to an IC$_{50}$ of approximately 10 μg/ml.

5. Synthesis and Anti-Microbial Activity of 2,3,4,5,6-pentaacetoxyxanthone

Although 2,3,4,5,6-pentahydroxyxanthone was found to have potent anti-malarial activity, the inventors postulated that the highly acidic nature of the 3 and 6 hydroxy groups of this compound (i.e. the $R_3$ and $R_6$ positions as shown in formula X1) could lead these groups to be highly ionized at physiological pH values. Such ionization would likely reduce the rate at which the compound could cross biological membranes, thereby lowering the uptake of the compound into parasitized erythrocytes. Accordingly, two derivatives of 2,3,4,5,6-pentahydroxyxanthone were produced which were expected to be more stable and uncharged above neutral pH: a pentacetoxy (i.e. esterified) derivative, 2,3,4,5,6-pentaacetoxyxanthone, as well as a methoxy (i.e. methyl ether) derivative, 2,3,4,5,6-pentamethoxyxanthone. The activity of these two derivatives against *P. falciparum* was measured.

As shown in Table 1, the addition of the ether (methoxy) groups essentially eliminated the anti-malarial activity of the compound, resulting in an IC$_{50}$ of >100 μM. This reduction in activity is believed to be attributable to the extreme stability of the methoxy groups; the methoxy group is less amenable to enzymatic cleavage under physiological conditions.

The pentaacetoxy derivative was produced by heating 2,3,4,5,6-pentahydroxyxanthone in acetic anhydride in the presence of a catalytic amount of sulfuric acid, followed by recrystallization. In contrast to the methoxy derivative, the esterified 2,3,4,5,6-pentaacetoxyxanthone was several times more potent than 2,3,4,5,6-pentahydroxyxanthone (exhibiting an IC$_{50}$ of approximately 0.075 μM). The enhanced activity of the esterified compound is postulated to be due to the ability of the compound to cross membranes (due to its neutral charge at physiological pH). Esters are also known to be amenable to enzymatic cleavage under physiological conditions. Accordingly, it is expected that the pentaacetoxyxanthone enters the cell where it is enzymatically cleaved to produce pentahydroxyxanthone.

6. Synthesis and Anti-Microbial Activity of 2,3,4,5,6,7-hexahydroxyxanthone

The newly discovered anti-malarial activity of 2,3,4,5,6-pentahydroxyxanthone prompted the investigation of other xanthones and related compounds. One such related compound was 2,3,4,5,6,7-hexahydroxyxanthone which was prepared using the following method:

2-hydroxy-3,4,5-trimethoxybenzoic acid (1.14 g, 0.005 mol) and 1,2,3,4-tetramethoxybenzene (0.99 g, 0.005 mol) and 25 ml of a 9% solution of P$_2$O$_5$ in methanesulfonic acid were shaken in a 50 ml cylindrical glass tube with a Teflon-lined screw-cap at room temperature for 54 hours. The dark orange mixture was then poured onto crushed ice (150 ml). After melting, the product was extracted with methylene chloride (3×40 ml). After removal of the solvent, the residue was chromatographed on silica gel (30 g) with CH$_2$Cl$_2$. Of the three fractions obtained (the eluent was monitored by thin-layer chromatography), the middle one was uniform and left pure 2-hydroxy-3,4,5,2',3',4',5'-heptamethoxybenzophenone (0.51 g, 25%) as a yellow oil upon evaporation of the solvent. This was dissolved in 100 ml 75% alcohol whereafter 5 ml of 10N NaOH were added and the mixture was heated to boiling in a beaker for three hours; the volume was kept at 100 ml by occasional addition of water. The mixture was then transferred to a 250 ml round bottom flask and refluxed for another 17 hours. After cooling, suction filtration yielded 0.36 g of 2,3,4,5,6,7-hexamethoxyxanthone as a white product (small needles, matted, 77%). In a deprotection procedure, similar to the one described above for pentamethoxyxanthone, 0.42 g of the hexamethoxyxanthone produced 0.296 g of hexahydroxyxanthone (91%) as a pale yellow powder. It was found advantageous to circumvent the need for centrifugation by stirring the methylene chloride-water mixture (from the quenching of the BBr$_3$-solution) in a wide-mouthed container for several hours, leading to the evaporation of the methylene chloride; the mixture is then easily filterable.

The antimalarial activity of 2,3,4,5,6,7-hexahydroxyxanthone was determined by the method described above. The IC$_{50}$ was determined to be 0.075 μM. The IC$_{50}$ of this compound against Leishmania was determined to be approximately 5 μM. The MIC of the compound against *Candida albicans* was determined to be approximately 37.5 μM, corresponding to an IC$_{50}$ of approximately 10 μg/ml.

7. Scope of Formula X1 Compounds

The inventors have discovered that a wide range of compounds related to 2,3,4,5,6-pentahydroxyxanthone have anti-microbial activity. These compounds can be represented by the formula X1 shown below.

wherein:

A is oxygen, substituted antimony (stibium), sulfur or N—R' wherein R' is H, OH, alkyl, haloalkyl, aryl or haloaryl; and

$R_1$–$R_8$ are independently selected from the group consisting of H, OH, halogen, aryl, arylamine, alkyl, substituted alkyl (such as alkylamine, alkylthio and haloakyl), amino, ester and nitro groups and O-linked and C-linked carbohydrates.

The activities of various formula X1 compounds against the *Plasmodium falciparum* parasite are shown in Table 1. The activities of various formula X1 compounds against *Leishmania donovani* are shown in Table 2. For comparison, Table 2 also shows the activity of stibogluconate, a standard anti-leishmanial. Other examples of specific formula X1 compounds are illustrated below:

2,3,4,5,6-pentahydroxythioxanthone 2,3,4,5,6-pentaacetoxythioxanthone 2,3,4,5,6-pentahydroxyacridone 2,3,4,5,6-pentaacetoxyacridone 2,3,4,5,6,7-hexaacetoxyxanthone 2,3,4,5,6,7-hexahydroxythioxanthone 2,3,4,5,6,7-hexaacetoxythioxanthone 2,3,4,5,6,7-hexaacetoxyacridone 2,3,4,5,6,7-hexahydroxyacridone 2,4,6,7-tetrahydroxy-3,6-acetoxyxanthone 2,4,5-trihydroxy-3,6-acetoxyxanthone

TABLE 1

| Compound Name | Xanthone Structure | IC$_{50}$, µM vs. Plasmodium |
|---|---|---|
| Xanthone | | 10 |
| Mangostin | | 5 |
| Mangiferin | | 50 |
| 3,4,5,6-Tetrahdroxy-xanthone | | 10 |
| 2,3,4,5,6-Pentahydroxy-xanthone | | 0.4 to 0.5 |
| 2,3,4,5,6,7-hexahydroxy-xanthone | | 0.075 |
| 2,3,4,5,6-Pentamethoxy-xanthone | | >100 |

TABLE 1-continued

| Compound Name | Xanthone Structure | IC$_{50}$, µM vs. Plasmodium |
|---|---|---|
| 2,3,4,5,6-Penta-acetoxyxanthone | [structure] | 0.075 |
| 1,2,3,5,6,7-Hexahydroxy-xanthone | [structure] | 25–50 |
| 1,3-dihydroxyxanthone | [structure] | >100 µM |
| 1,3,5,6,7-pentahydroxy-xanthone | [structure] | 1 µM |

TABLE 2

| Compound | IC$_{50}$, mg/ml vs. Leishmania |
|---|---|
| [structure] 2,3,4,5,6-Pentahydroxyxanthone "X5" | 0.0015 |
| [structure] 2,3,4,5,6,7-hexahydroxyxanthone "X6" | 0.0015 |

TABLE 2-continued

| Compound | $IC_{50}$, mg/ml vs. Leishmania |
|---|---|
| <br>Mangostin | 0.00041 |
| <br>Mangiferin | >0.05 |
| <br>Sodium Antimonyl (V) Gluconate<br>"Stibogluconate"<br>Stibogluconate | 0.1 to 1.0* |

*taken from literature values

8. Sources of Formula X1 Compounds and Preferred Method of Synthesis

Many xanthones and xanthone derivatives can be purchased commercially from sources including: ICN Biomedicals, Irvine, Calif.; Sigma Chemical Company, St. Louis, Mo.; Aldrich Chemical Company, Milwaukee, Wis.; Janssen Chimica (Belgium). In addition, many xanthones are naturally occurring compounds which can be purified by methods such as those described in Hostettmann et al. (1995).

A. General method of xanthone synthesis

Xanthones according to the present invention may be synthesized by the general method described above, for the synthesis of 2,3,4,5,6,7-hexahydroxyxanthone and 2,3,4,5, 6-pentahydroxyxanthone. Essentially, this method comprises subjecting an o-hydroxy-o'-methoxy-benzophenone to base treatment (e.g., aqueous sodium hydroxide), which leads to the formation of the central oxygen-bridged ring; the o-phenoxide (from the o-hydroxyl in basic medium) then replaces the methoxide on the other ring by nucleophilic substitution. The net effect is expulsion of $CH_3O^-$, and the formation of a diphenyl ether. Since the two phenyl rings are already linked by a carbonyl group, a xanthone is obtained. The o—OH,o'—$OCH_3$ groupings are required for this reaction; although the methyl could be replaced with other groups, this is not likely to be of any advantage since methyl ethers are readily available. However, other substituents can be present in the two aromatic rings of the benzophenones. For example, for the synthesis of the penta- and hexa- hydroxyxanthones described above, these other substituents were methoxy groups.

The benzophenones used in synthesizing the xanthones as described above may be obtained by combining substituted benzoic acids and methoxybenzenes by a condensation or other coupling procedure. In an exemplary condensation procedure, the benzoic acid carries an o-hydroxy group:

This coupling can be achieved by condensation in polyphosphoric acid or a mixture of phosphorus pentoxide and methanesulfonic acid. Alternatively, benzophenones may be synthesized by Friedel-Crafts acylation (of a benzoyl chloride and a polymethoxybenzene), or by the Hoesch synthesis, or by reaction of a benzoyl chloride with an appropriately metalated (e.g., lithiated) aromatic.

In particular cases, additional substituents may be introduced into the benzophenone after the benzophenone has been synthesized.

Alternatively, xanthones may be derived from benzophenones by oxidative cyclization. This method essentially requires an o-hydroxy group on one ring and a free position (occupied by H) on the other ring. Oxidation (e.g., with $K_3[Fe(CN)_6]$, or $KMnO_4$) produces an oxygen bridge with the elimination of 2H.

B. Synthesis of Thioxanthones

Thioxanthones may be obtained by a number of methods. Exemplary syntheses include: (1) combining an o-mercaptobenzoic acid with a halobenzene (preferably iodo or bromo); and (2) combining an o-halobenzoic acid (preferably either bromo or iodo) with a mercaptobenzene. The intermediate diphenylsulfide produced in each case is then condensed to yield the required thioxanthone as illustrated in the following schematic:

Methods of synthesizing thioxanthones using this general reaction scheme are described in Hollis-Showalter et al., *J. Med. Chem.* 31, 1527 (1988).

C. Synthesis of Acridones

Acridones may be synthesized by a number of different methods. The following methods are exemplary and are well known in the art.

Acridones may be formed from o-nitrobenzophenones, which are reduced to obtain o-aminobenzophenones which are in turn cyclized with either o'-methoxy or o'-hydroxy groups to produce the acridones. The o-nitrobenzophenones which are used as starting materials may be obtained either by Friedel-Crafts acylation of phenols or methoxybenzenes using o-nitrobenzoylchlorides, or by direct nitration of benzophenones, or by coupling of lithiated arenes with o-nitrobenzol chlorides (e.g., as described by Parkham et al., *Journal of Organic Chemistry* 46, 1057 (1981). An exemplary synthesis is illustrated below:

Alternatively, o-nitrobenzophenones may be formed by coupling of 2-methyl-3,1-benzoxazin-4-ones (from o-aminobenzoic acid by heating with acetic anhydride) with aromatic Grignard reagents (e.g., Adams et al. *J.C.S. Perkin Trans I* 2089 (1976)).

Alternatively, acridones may be produced by zinc chloride catalyzed condensation of hydroxyanthranilic acids and polyhydroxybenzenes (such as described by Bahar et al., *Phytochemistry* 21, 2729 (1982)) and illustrated in the following scheme:

-continued

Acridones may also be formed by cycloaddition of derivatives of anthranilic acids with dehydrobenzenes such as described by Khanapure et al., *Tetrahedron Letters* 31:2869 (1990).

D. Deprotection

Deprotection of polymethoxyxanthones, polymethyoxythioxanthones or polymethoxyacridones may be achieved in a number of ways, including treating with either hydriodic acid or with a methylene chloride solution of boron tribromide, and hydrolysis of the intermediate boronphenoxy compound.

9. Activity of Formula X1 Compounds

The formula X1 compounds according to the present invention are useful in inhibiting the growth of microbial pathogens, including protozoan parasites (for example, Plasmodium sp. and Leishmania sp.) and yeast (for example, *Candida albicans*). Thus, one aspect of the present invention is a method of inhibiting the growth of a microbial pathogen by contacting the microbial pathogen with a formula X1 compound. In this context, it is, of course, necessary to contact the microbial pathogen with a sufficient amount of the formula X1 compound to inhibit growth of the pathogen. One skilled in the art will readily appreciate that the amount of compound sufficient to inhibit the growth of the microbial pathogen will vary according to the formula X1 compounds selected, the target microbial pathogen and the environment in which the microbial pathogen is growing. Standard methods are available for determining the $IC_{50}$ concentration of formula X1 compounds for microbial pathogens in vitro. Alternatively, $ED_{50}$ values may be determined in an animal. See Munson, Principles of Pharmacology (Chapman and Hall, 1995) Chapter 1. Exemplary $IC_{50}$ values (showing activities against Plasmodium and Leishmania, respectively) are presented in Tables 1 and 2. These values relate to the inhibition of a microbial pathogen grown in vitro. Contacting the microbial pathogen with a compound according to formula X1 may also be performed in vivo where necessary to inhibit the growth of microbial pathogens under physiological conditions. The following section addresses compositions and dosages appropriate for inhibiting the growth of microbial pathogens in such circumstances.

10. Pharmaceutical Compositions

Formula X1 compounds having anti-microbial activity are administered to patients in conventional dosage forms prepared by combining an appropriate dose of the compound with standard pharmaceutical carriers. Suitable pharmaceutical carriers may be, for example, solids or liquids. Suitable solid carriers include lactose, magnesium stearate, terra alba, sucrose, talc, stearic acid, gelatin, agar, pectin, acacia and cocoa butter. The amount of solid carrier will vary widely depending on which carrier is selected, but preferably will be from about 25 mg to about 1 g. Suitable liquid carriers include syrup, peanut oil, olive oil, sesame oil, propylene glycol, polyethylene glycol and water. The carrier or diluent may also include time delay material well known to the art such as, for example, glyceryl, monostearate or glycerol distearate, either alone or with a wax. The foregoing examples of suitable pharmaceutical carriers are only exemplary and one of skill in the art will recognize that a very wide range of such carriers may be employed.

The formulation of the formula X1 compound with a pharmaceutical carrier can take many forms. For example, the formulation may be a tablet, capsule, powder, suppository, lozenge, syrup, emulsion, liquid suspension or solution, or sterile injectable liquid. The pharmaceutical compositions are prepared by conventional techniques involving procedures such as mixing, granulating and compressing, and dissolving the ingredients. As will be appreciated from the foregoing exemplary formulations, administration of the compounds can be by any known route, including oral administration, intramuscular and intravascular injection.

The methods of treating a patient suffering from a microbial disease, such as malaria, in accordance with this invention comprise administering to the patient a therapeutically effective amount of a compound according to formula X1. Preferably, the patient will be administered the formula X1 compound in a formulation as described above (i.e. in combination with a pharmaceutical carrier), the formulation having a therapeutically effective amount of the formula X1 compound.

As used herein, "a therapeutically effective amount" is preferably an amount that results in complete remission of the disease. However, it will be recognized that any improvement in the patient's condition is clinically advantageous. Hence, "a therapeutically effective amount" also encompasses amounts of the administered compound that result in partial remission of the disease or which slow or limit the further progression of the disease, or which inhibit the growth of the infectious agent or which reduce the clinical signs and symptoms of the disease (for example, fever and chills in a malaria infection). It is anticipated that therapeutically effective dosages which slow or limit the spread of the disease, or which inhibit the growth of the parasite will be particularly suitable for combination with other anti-microbial drugs.

The compounds of the invention can be administered in a daily dosage schedule of from about 10 mg to about 10 g. One skilled in the art will recognize that in determining the active amount of the anti-microbial compound to be administered, the activity of the specific compound selection, the age, weight and condition of the patient and the administration of other drugs to the patient must be considered.

REFERENCES

Heyneman, D. (1988), The Worldwide Burden of Parasitic Disease, in *Parasitic Infections*, J. Leech, M. Sande and R. Root, Eds. Churchill Livingstone: New York. pp. 11–32.

World Health Organization (1991), United Nations Development Program/WorldBank/WHO Special Programme for Research and Training in Tropical Diseases. Tropical diseases: progress in research, 1989–1990:29–40.

Campbell, W. (1986), The chemotherapy of parasitic infections, *J. Parasitol.*, 72:45–61.

Mebrahtu, Y., P. Lawyer, J. Githure, J. B. Were, R. Muigai, L. Hendricks, J. Leeuwenburg, D. Koech, and C. Roberts (1989), Visceral leishmaniasis unresponsive to pentostam caused by *Leishmania tropica* in Kenya. *Am. J. Trop. Med. Hyg.*, 41:289–94.

Grogl, et al. (1992) *Am. J. Trop. Med. Hyg.* 47:117–126.

Cowman, A. F. and S. J. Foote (1990), Chemotherapy and drug resistance in malaria, *Int. J. Parasitol.*, 20:503–13.

Larrey, D. (1989), Exifone: a new hepatotoxic drug, *Gastroenterol. Clin. Biol.*, 13:333–334.

Elabbadi, N., M. Ancelin, and H. Vial (1992), Use of radioactive ethanolamine incorporation into phospholipids to assess in vitro antimalarial activity by the semiautomated microdilution technique. *Antimicrob. Agents Chemother.*, 36:50–55.

Atamna, H., and H. Ginsburg (1993), Origin of reactive oxygen species in erythrocytes infected with *Plasmodium falciparum* [published erratum appears in *Mol. Biochem. Parasitol.* (1994) 63:312], *Mol. Biochem. Parasitol.* 61:231–41.

Brodie, B., J. Axelrod, P. Shore, and S. Udenfriend (1954), Ascorbic acid in aromatic hydroxylation. II. Products formed by reaction of substrates with ascorbic acid, ferrous ion, and oxygen, *J. Biological Chemistry* 208:741–749.

Maissant, J., C. Bouchoule, P. Canesson, and M. Blanchard (1983), Hydroxylation des composés aromatiques par le système d'Udenfriend: Remplacement de l'acide ascorbique par une réduction électrochimique, *Journal of Molecular Catalysis* 18:189–192.

Udenfriend, S., C. Clark, J. Axelrod, and B. Brodie (1954), Ascorbic acid in aromatic hydroxylation. I. A model system for aromatic hydroxylation, *J. Biol. Chemistry* 208:731–739.

Grover, P., G. Shah, and R. Shah (1955), *J. Chem. Soc.*:3982 and Grover, P., G. Shah, and R. Shah (1956), Xanthones: Part V-A new synthesis of Lichexanthone. 15B. *J. Sci. Indust. Res.* 629–633.

Aust, S., M. L A, and C. Thomas (1985), Role of metals in oxygen radical reactions. *Journal of Free Radicals in Biology and Medicine* 1:3–25.

Goldstein, D., D. Meyerstein, and G. Czapski (1993), The Fenton Reagents. *Free Radical Biology and Medicine* 15:435–445.

Hambloch and Frahm (1984) *Eur. J. Med. Chem.—Chim. Ter.* 20:71–77.

Ghosal et al. (1978) *J. Pharm. Sci.* 67:721–722.

Cooper et al. (1992) *J. of Antibiotics* 45:444–453.

Wang and Liu (1994) *J. Natural Products* 57:211–217.

Sultanbawa (1980) *Tetrahedron* 36:1465–1506.

Hostettmann et al. (1995) in *Phytochemistry of Plants Used In Traditional Medicine*, chapter 2, (Hostettmann et al. ed) Oxford Science Publications.

Mayer and Fikentscher (1956) *Chem. Ber.* 89:511.

What is claimed is:

1. A method of inhibiting the growth of a protozoan parasite, the method comprising the steps of:

providing a therapeutically effective amount of a composition comprising a compound having a formula wherein A is oxygen, and $R_1$–$R_8$ are independently selected from the group consisting of H, OH, aryl, arylamine, alkyl, substituted alkyl, halogen, amino, ester and nitro groups, and O-linked and C-linked carbohydrates; and contacting the protozoan parasite with the compound thereby inhibiting parasite growth.

2. The method of claim 1 wherein in the formula $R_1$ and $R_8$ are H.

3. The method of claim 1 wherein the step of contacting the parasite with the compound comprises administering a therapeutically effective dosage of the compound to a patient infected with the parasite.

4. The method of claim 1 wherein the protozoan parasite is a Plasmodium sp. or a Leishmania sp.

5. A method of inhibiting the growth of a protozoan parasite, the method comprising contacting the parasite with an amount of a compound selected from the following group, the amount sufficient to inhibit the growth of the parasite: 2,3,4,5,6-pentahydroxyxanthone; 2,3,4,5,6-pentaacetoxyxanthone; 2,3,4,5,6,7-hexahydroxyxanthone; 2,3,4,5,6,7-hexaacetoxyxanthone.

6. The method of claim 5 wherein the protozoan parasite is selected from the group consisting of: *Leishmania donovani, Plasmodium falciparum, Giardia lamblia, Trypanosoma gambiense, Trypanasoma cruzi, Cryptosporidium parvum, Entamoeba histolytica, Pneumocystis carinii*, and *Toxoplasmosis gondii*.

* * * * *